United States Patent [19]
Forssen et al.

[11] Patent Number: 5,888,537
[45] Date of Patent: *Mar. 30, 1999

[54] VINCA ALKALOID VESICLES WITH ENHANCED EFFICACY AND TUMOR TARGETING PROPERTIES

[75] Inventors: Eric Forssen, La Canada; Gerry Cox, Chino Hills; Dennis Hair, Alhambra, all of Calif.

[73] Assignee: NeXstar Pharmaceuticals, Inc., Boulder, Colo.

[*] Notice: The term of this patent shall not extend beyond the expiration date of Pat. No. 5,714,163.

[21] Appl. No.: 937,935

[22] Filed: Sep. 25, 1997

Related U.S. Application Data

[60] Division of Ser. No. 389,663, Feb. 16, 1995, Pat. No. 5,714,163, which is a continuation-in-part of Ser. No. 266,059, Jun. 27, 1994, abandoned.

[51] Int. Cl.$^6$ .......................... A61K 9/127; A61K 9/133
[52] U.S. Cl. .................................................. 424/450
[58] Field of Search ............................................. 424/450

[56] References Cited

U.S. PATENT DOCUMENTS

| | | |
|---|---|---|
| 4,769,250 | 9/1988 | Forssen . |
| 4,963,363 | 10/1990 | Forssen . |
| 5,019,369 | 5/1991 | Presant et al. . |
| 5,080,904 | 1/1992 | Iga et al. . |
| 5,316,771 | 5/1994 | Barenholz et al. . |
| 5,456,916 | 10/1995 | Kurata et al. . |
| 5,714,163 | 2/1998 | Forssen ................................. 424/450 |

FOREIGN PATENT DOCUMENTS

| | | |
|---|---|---|
| 8601102 | 2/1986 | WIPO . |
| 9015595 | 12/1990 | WIPO . |
| 9300888 | 1/1993 | WIPO . |

OTHER PUBLICATIONS

Boman et al., "Optimization of the retention properties of vincristine in liposome systems," *Biochimica et Biophysica Acta* 1152:253–258, 1993.

Boman et al., "Liposomal vincristine which exhibits increased drug retention and increased circulation longevity cures mice bearing P388 tumors," *Cancer Research* 54:2830–2833, 1994.

Forssen et al., "Liposome–entrapped vincristine and mitomycin–C for treatment of solid tumors: in vivo efficacy as a function of co–entrapped counterion," Abstract, *Proc. Am. Assoc. Cancer Res.* 34:365, 1993.

Layton and Trouet, "A comparison of the therapeutic effects of free and liposomally encapsulated vincristine in leukemic mice," 16:945–950, (1980).

Mayer et al., "Identification of vesicle properties that enhance the antitumour activity of liposomal vincristine against murine L1210 leukemia," *Cancer Chemother Pharmacol* 33:17–24, 1993.

Vaage et al., "Therapy of mouse mammary carcinomas with vincristine and doxorubicin encapsulated in sterically stabilized liposomes," *Int. J. Cancer* 54:959–964, 1993.

*Primary Examiner*—Gollamudi S. Kishore
*Attorney, Agent, or Firm*—Swanson & Bratschun LLC

[57] ABSTRACT

A liposome formulation containing a Vinca Alkaloid and an anion in an aqueous phase of the liposome. The liposomes also comprise distearoylphosphatidyl choline, cholesterol and disteraroylphosphatidylglycerol. A method for enhancing the efficacy and tumor targeting properties of liposomal vinca alkaloid formulations containing unilamellar vesicles.

12 Claims, 2 Drawing Sheets

VINCA ALKALOID VESICLES WITH ENHANCED EFFICACY AND TUMOR TARGETING PROPERTIES

This is a divisional application Ser. No. 08/389,663 filed on Feb. 16, 1995, now U.S. Pat. No. 5,714,163 which is a CIP of Ser. No. 08/266,059 filed Jun. 27, 1994, now abandoned

FIELD OF THE INVENTION

This invention relates to the fields of biochemistry and medicine, and particularly to a pharmaceutical preparation which includes liposome-entrapped water soluble drug formulations, and methods of using such formulations to control the delivery of encapsulated agents to tumors in mammals, including humans.

BACKGROUND OF THE INVENTION

Important anti-tumor agents exist known as dimeric catharanthus alkaloids also known as the vinca alkaloids. The vinca alkaloids are obtained from the fractionation of extracts of the Periwinkle Plant (*Vinca rosea*) which is a species of myrtle. There are four generally known extracts that are active dimeric alkaloids which include vinblastine, vincristine, vinleurosine and vinrosidine. Vinblastine and vincristine are the two most common and important clinical agents. Vinblastine is primarily used in combination with bleomycin and cisplatin in the treatment of metastatic testicular tumors. Vinblastine also promotes beneficial responses in lymphoma and is active in Kaposi's sarcoma, neuroblastoma, and Letterer-Siwe disease (Histiocytosis X). It is also known to be active in carcinoma of the breast and choriocarcinoma in women.

Vincristine is the preferred treatment in childhood leukemia. Vincristine also has similar clinical activity to that of vinblastine. For example vincristine is effective in the treatment of Hodgkin's Disease. It is also useful in non-Hodgkin's lymphoma when used in combination with such agents as bleomycin and doxorubicin. Vincristine is also used to elicit responses in patients with neoplasms such as Wilms' tumor, neuroblastoma, brain tumors, rhabdomyosarcoma, carcinoma of the breast, bladder and tumors that present themselves in male and female reproductive systems. Vincristine is also used in combination with doxorubicin and bleomycin in the treatment of Kaposi's sarcoma. The effectiveness of the vinca-alkaloids is in their ability to cause mitotic arrest at metaphase in dividing cells during the cell cycle, thus arresting cell division in metaphase. Although the above agents have been effective as anti-cancer agents there have been associated with the use of these agents serious cytotoxic effects on normal cells. For example, bone-marrow depression is common. Neurotoxicity is another serious side effect associated with Vincristine. Alopecia and hair loss are also associated with the use of vinblastine and vincristine. Other toxicities include anemia, polyuria, dysuria, gastrointestinal irregularities, thrombocytopenia and cardiotoxicity.

In an effort to decrease the toxicity of the vinca-alkaloids and to increase their therapeutic effectiveness, workers have attempted to utilize liposomal formulations of vincristine and vinblastine to overcome these problems.

Liposomes are microscopic vesicles made, in part, from phospholipids which form closed, fluid filled spheres when dispersed with water. Phospholipid molecules are polar, having a hydrophilic ionizable head group and two hydrophobic tails consisting of long fatty acid chains. Thus, when sufficient phospholipid molecules are present with water, the tails spontaneously associate to exclude water while the hydrophilic phosphate heads interact with water. The result is a bilayer membrane in which the fatty acid tails converge in the newly formed membrane's interior and the polar heads point in opposite directions toward an aqueous medium. These bilayer membranes can be caused to form closed spheres known as liposomes. The polar heads at the inner surface of the membrane point toward the aqueous interior of the liposome. At the opposite surface of the spherical membrane, the polar heads interact with the surrounding aqueous medium. As the liposomes are formed, water soluble molecules can be incorporated into the aqueous interior, and lipophilic molecules will tend to be incorporated into the lipid bilayer. Liposomes may be either multilamellar, like an onion with liquid separating many lipid bilayers, or unilamellar, with a single bilayer surrounding an entirely aqueous liquid center.

There are many types of liposome preparation techniques which may be employed and which produce various types of liposomes. These can be selected depending on the use, the chemical intended to be entrapped, and the type of lipids used to form the bilayer membrane. The requirements which must be considered in producing a liposome preparation are similar to those of other controlled release mechanisms. They are as follows: (1) high percent of chemical entrapment; (2) increased chemical stability; (3) low chemical toxicity; (4) rapid method of production; and (5) reproducible size distribution.

The first method described to encapsulate chemicals in liposomes involved production of multilamellar vesicles (MLVs). Methods for encapsulating chemicals in MLVs are known in the art.

Liposomes can also be formed as unilamellar vesicles (UVs), which generally have a size less than 1 $\mu$m. There are several techniques known in the art which are used to produce unilamellar liposomes.

Smaller unilamellar vesicles can be formed using a variety of techniques. By dissolving phospholipids in ethanol and injecting them into a buffer, the lipids will spontaneously rearrange into unilamellar vesicles. This provides a simple method to produce UVs which have internal volumes similar to that of those produced by sonication (0.2–0.5 L/mol/lipid). Sonication, extrusion (through filters) of MLVs also results in dispersions of UVs having diameters of up to 0.2 $\mu$m, which appear as clear or translucent suspensions.

Another common method for producing small UVs is the detergent removal technique. Phospholipids are solubilized in either ionic or non-ionic detergents such as cholates, Triton X, or n-alkylglucosides. The drug is then mixed with the solubilized lipid-detergent micelles. Detergent is then removed by one of several techniques: dialysis, gel filtration, affinity chromatography, centrifugation, ultrafiltration. The size distribution and entrapment efficiencies of the UVs produced this way will vary depending on the details of the technique used.

Smaller unilamellar vesicles can be formed using a variety of techniques, such as applying a force sufficient to reduce the size of the liposomes and or produce smaller unilamellar vesicles. Such force can be produced by a variety of methods, including homogenization, sonication or extrusion (through filters) of MLV's. These methods result in dispersions of UVs having diameters of up to 0.2 $\mu$m, which appear as clear or translucent suspensions. Other standard methods for the formation of liposomes are know in the art, for example, methods for the commercial production of liposomes include the homogenization procedure described in U.S. Pat. No. 4,753,788 to Gamble, a preferred technique, and the method described in U.S. Pat. No. 4,935,171 to Bracken, which are incorporated herein by reference.

The therapeutic use of liposomes includes the delivery of drugs which are normally toxic in the free form. In the liposomal form the toxic drug may be directed away from the sensitive tissue and targeted to selected areas. Liposomes can also be used therapeutically to release drugs, over a prolonged period of time, reducing the frequency of administration. In addition, liposomes can provide a method for forming an aqueous dispersion of hydrophobic drugs for intravenous delivery.

When liposomes are used to target encapsulated drugs to selected host tissues, and away from sensitive tissues, several techniques can be employed. These procedures involve manipulating the size of the liposomes, their net surface charge as well as the route of administration. More specific manipulations have included labeling the liposomes with receptors or antibodies for particular sites in the body. The route of delivery of liposomes can also affect their distribution in the body. Passive delivery of liposomes involves the use of various routes of administration, e.g., intravenous, subcutaneous and topical. Each route produces differences in localization of the liposomes. Two common methods used to actively direct the liposomes to selected target areas are binding either antibodies or specific receptor ligands to the surface of the liposomes. Antibodies are known to have a high specificity for their corresponding antigen and have been shown to be capable of being bound to the surface of liposomes, thus increasing the target specificity of the liposome encapsulated drug.

Since the chemical composition of many drugs precludes their intravenous administration, liposomes can be very useful in adapting these drugs for intravenous delivery. Many hydrophobic drugs, fall into this category because they cannot be easily dissolved in a water-based medium and must be dissolved in alcohols or surfactants which have been shown to cause toxic reactions in vivo. Liposomes, composed of lipids, with or without cholesterol, are nontoxic. Furthermore, since liposomes are made up of amphipathic molecules, they can entrap hydrophilic drugs in their interior space and hydrophobic molecules in their lipid bilayer. Although methods for making liposomes are well known in the art, it is not always possible to determine a working formulation without undue experimentation.

Efforts have been made to increase the therapeutic ability of anticancer or antineoplastic drugs in general and vincristine in particular. Efforts have also been made to reduce the toxic side effects associated with the use of these agents. Further, work has been done to increase the circulation time and accumulation in tumors of the various agents encapsulated within the liposomes. Examples of the work that has been done with tumor uptake is discussed in U.S. Pat. No. 5,019,3692 and U.S. application Ser. No. 07/835931 filed on Jul. 3, 1991 (PCT); both of these documents are incorporated by reference. Specific work performed on liposomal vincristine is also shown in references such as D. Layton and A. Trouet, *Europ. J Cancer* (1980) 16:945–50; J. Vaage et al., *Int. J Cancer* (1993) 54:/959–64; and L. D. Mayer et al., *Cancer Chemother. Phamacol.* (1993) 33:/7–24. Much work remains to be done in developing liposomal formulations which are stable on storage and which are capable of enhanced tumor targeting.

Thus, it is a desideratum to provide for a liposomal formulation with enhanced tumor targeting properties and which provides an increase in therapeutic value over free drug and offers decreased toxicity. It is an object of the invention to provide a liposomal formulation that is stable in that the formulation will not aggregate over time.

SUMMARY OF THE INVENTION

The invention comprises liposomes having an internal aqueous space with a defined pH and comprised of a phosphatidylcholine and cholesterol in a ratio of about 2:1 (mole ratio) and having a median size of less than 100 nm. The liposomes further comprise a cationic vinca alkaloid and an anion of low membrane permeability within the aqueous phase. An embodiment of the invention comprises a preferred alkaloid to lipid ratio between about 1:200 and 1:50 (w/w), pH of the internal aqueous phase between about 4.0–8.0, and liposomes that retain their contents for a period of greater than 20 weeks at 4° C. and do not aggregate. A preferred embodiment comprises an internal aqueous phase having a pH between about 5.0 and 6.5 preferable at about 5.5.

In another aspect of the invention the liposomes are comprised of a phosphatidylcholine, cholesterol, and a negatively charged lipid in a molar ratio sufficient to prevent aggregation of the liposomes on storage wherein the liposomes retain their contents for a period of greater than 20 weeks at 4° C.

A significant benefit of these formulations is that they can be prepared without a transmembrane or pH gradient. Thus, according to the practice of the invention, the liposomes are preferably suspended in a medium having the same pH as the pH of the internal aqueous phase of the liposomes.

In one aspect of the invention, a method is provided for enhancing the tumor targeting properties of liposomes by including in the liposome an anion of low membrane permeability and a negatively charged lipid.

DETAILED DESCRIPTION OF THE INVENTION

Figure 1:
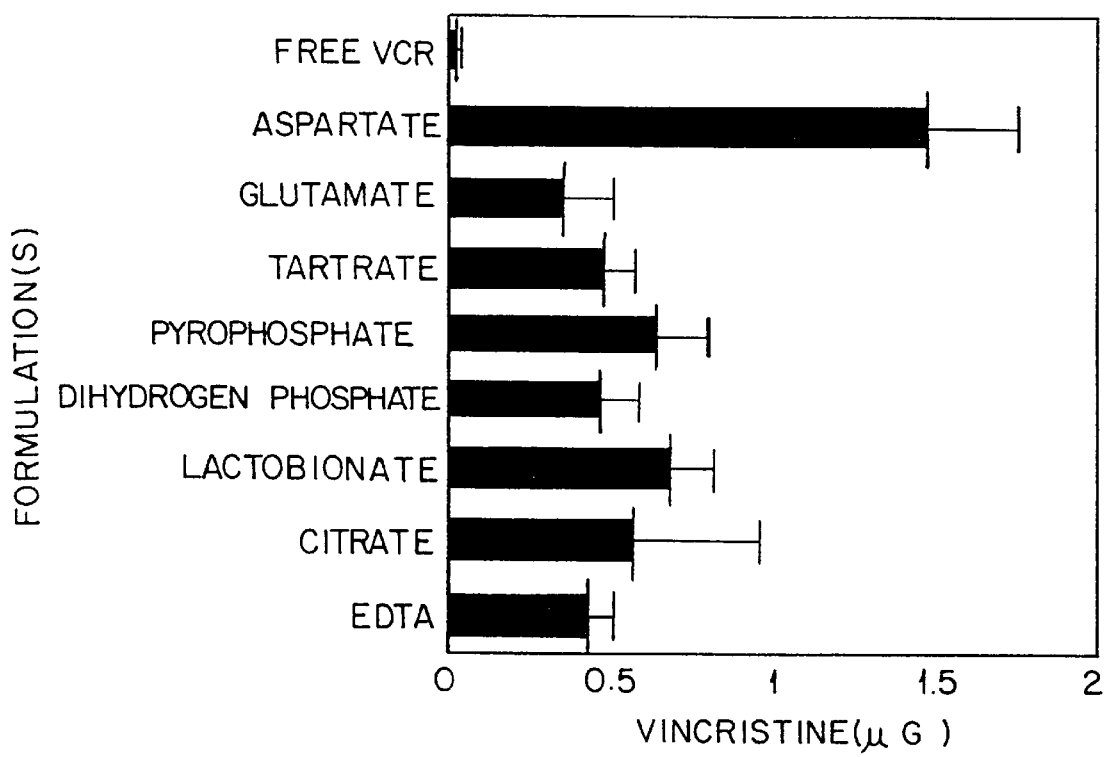
FIG. 1 displays the amount of vincristine taken up in the tumor of mice using neutral liposomes.

As used herein, the term liposome refers to unilamellar vesicles or multilamellar vesicles such as described in U.S. Pat. Nos. 4,753,788 and 4,935,171, the contents of which are incorporated herein by reference.

Liposomes are formed by first forming a spray dried powder of a phosphatidylcholine (PC) and cholesterol (CHOL) in a molar ratio of about 2:1. The preferred phosphatidylcholine is distearoyl phosphatidylcholine (DSPC). Other PCs may be used such as a phosphatidylcholine having a carbon chain length of from 14–20, preferably 16–18 carbon atoms. Such phosphatidylcholines include dilaurylphosphatidylcholine (DLPC), dipalmitoylphosphatidylcholine (DPPC), and dimiristoylphosphatidylcholine (DMPC).

The anion is selected from either an organic salt or an inorganic salt. Preferred anions include glutamate, tartrate, phosphate, EDTA, succinate, aspartate, pyrophosphate, lactobionate, citrate, and sulfate. For tumor uptake enhancement the most preferred anions are lactobionate and aspartate, the most preferred being aspartate.

Vincristine (Vcr) containing liposomes were prepared by ion exchange loading processes in which the salt of a negative counterion (a lipid-membrane-impermeable species of charge opposite to Vcr) and a small molecular weight, positive exchange-ion (lipid-membrane-permeable) are first entrapped within the vesicle. During the entrapment process, the exchange ion escapes from the liposomes in exchange for Vcr. Vcr enters the liposomes, gaining charge balance and forming a salt with the counterion. Selection of a counterion for Vcr entrapment is dependent upon several considerations including: 1) physiological acceptability; 2) buffering at a pH acceptable for Vcr stability; and 3) ability to retain the entrapped Vcr within the liposomes.

In another aspect of the invention a method is provided for the administration of a therapeutic effective amount of liposome having an internal aqueous space with a defined pH and comprised of a phosphatidylcholine and cholesterol in a molar ratio of about 2:1 and having a median size of less than 100 nm wherein the liposomes further comprise a cationic vinca alkaloid and an anion of low membrane permeability within the aqueous phase. The liposome further comprises a negatively charged lipid for further enhancing tumor up-take and vesicle stability.

Further preferred embodiments include negatively charged liposomes comprised of a cationic alkaloid and an anion of low membrane permeability within an aqueous phase of the liposome wherein the alkaloid to lipid ratio (w/w) is between about 1:200 and 1:50, the most preferred range at about 1:100 to about 1:150, the preferred being about 1:100. However, when methylammonium is used, the preferred ratio is about 1:150. The negatively charged liposomes comprise DSPC, CHOL, and a negatively charged lipid in a ratio of about 2:1:0.01 to about 2:1:0.5. The preferred negatively charged lipid consists of a phosphatidylglycerol having a carbon chain length of from 16–20 including dilaurylphosphatidylglycerol (DLPG), dimyristoylphosphatidylglycerol (DMPG), distearoyl phosphatidylglycerol (DSPG), and dipalmitoylphosphatidylglycerol (DPPG). The preferred formulation is DSPC:CHOL:DSPG in a molar ratio of 2:1:0.1.

Another preferred aspect of the invention is a method which provides for the enhancement of tumor targeting and uptake by the delivery of a therapeutic amount of liposomes to a mammal including humans wherein the liposomes have an internal aqueous space with a defined pH and comprised of DSPC:CHOL:DSPG in a mole ratio of about 2:1:0.1 and further having a median size of less than 100 nm and preferably between 30–70 nm wherein the liposomes further comprise vincristine and aspartate wherein the vincristine to lipid ratio is preferably 1:100 and the pH of the internal aqueous phase is between about 5.0–6.0, preferably at about 5.0 wherein the liposomes retain their contents for a period greater than 20 weeks at 4° C. The preferred negatively charged formulations are surprisingly more efficacious than their neutral counterparts.

Since the dosage regimens for vincristine and vinblastine are well known to medical practitioners, the amount of the liposomal formulations which is effective for the treatment of infections in mammals and particularly humans will be apparent to those skilled in the art.

While we do not wish to be bound to any particular theory underlying the invention, it is hypothesized that potential mechanisms may include alterations in physical properties or pharmacological activities. Physically, while entrapped in the vesicle, a particular salt form could exist free in solution or as a precipitate; this could be anticipated for mono- and multivalent counterions, respectively. Thus, as the vesicle carrier breaks down in vivo, there could be a prolonged localization of material at the site of release, depending upon its solubility. Precipitated materials, for example, may be retained at the tumor site or within sensitive tissues, resulting in an enhanced antineoplastic effect or increased toxicities, respectively. The counterion may also affect interactions between the drug and the lipid membrane, altering stability (leakage) while in the circulation or biodistribution at the tissue or subcellular levels. The pharmacological effects may be more complex to elucidate. Significant synergistic or antagonistic effects may occur if the counterion is a chelator, amino acid, metabolite or if has an effect upon cellular metabolism at the delivery site.

This invention will be more fully understood by reference to the following examples, which are intended to be illustrative of the invention, but not limiting thereof.

EXAMPLE 1

This example details the entrapment of vincristine into neutral vesicles, e.g., distearoylphosphatidylcholine:cholesterol, 2:1 molar ratio. This example further details the efficacy of neutral liposomes. Vesicles were prepared by hydrating approximately 500 mg of sprayed-dried lipids, DSPC:CHOL (2:1, mole ratio), at 65° C. with either a buffer containing the ammonium salt of one of the counterions or 300 mM sucrose. The lipid concentration was approximately 100 mg/ml. The hydrating buffers consisted of (1) 150 mM ammonium glutamate; (2) 100 mM ammonium tartrate; (3) 150 mM ammonium dihydrogen pyrophosphate; (4) 150 mM ammonium aspartate; (5) 100 mM ammonium ethylenediaminetetraacetic acid; (6) 100 mM ammonium succinate; (7) 100 mM ammonium pyrophosphate; (8) 150 mM concentration ammonium lactobionate; (9) 75 mM ammonium citrate; and (10) ammonium sulfate. The hydrated lipids were sonicated at 65° C. for about 20 minutes with a probe sonicator. The vesicles were annealed for 10 minutes at 65° C., cooled to room temperature (RT), centrifuged 10 minutes at 3500 RPM, and subjected to a buffer exchange by gel filtration on a 60 cm G50–80 Sephadex column previously equilibrated with unbuffered 300 mM sucrose. Concentration of the lipids was determined by HPLC. The liposomes were then stored at room temperature overnight.

Vcr was added as an aqueous solution of its sulfate salt to the preformed liposomes yielding a drug to phospholipid ratio of 1 mg Vcr to 40–50 mg of phospholipid. The pH of the solution was adjusted to 7 with 1N NaOH. The resulting solution was incubated for 10 minutes at 65° C. Unentrapped Vcr was removed by gel filtration on a Sephadex G50–80 column and the liposomal Vcr was sterile-filtered. Vcr concentrations were determined by either a UV spectrophotometric assay or by HPLC. The vesicle characteristics are displayed in Table 1.

TABLE 1

Vcr Vesicle Characteristics

| Counterion | % Vcr | pH | Vcr (mg/ml) HPLC | Lipid: Vcr | LSI | Diameter (nm) |
|---|---|---|---|---|---|---|
| Glutamate | 84.2 | 6.99 | 0.303 | 56.0 | 3.7 | 46 |
| Tartrate | 90.9 | 7.02 | 0.366 | 51.5 | 4.3 | 54 |
| Dihyrogen phosphate | 81.4 | 7.12 | 0.270 | 58.6 | 4.4 | 45 |
| Aspartate | 80.5 | 7.23 | 0.298 | 54.1 | 4.2 | 49 |
| EDTA | 79.7 | 7.38 | 0.312 | 53.9 | 4.2 | 51 |

TABLE 1-continued

Vcr Vesicle Characteristics

| Counterion | % Vcr | pH | Vcr (mg/ml) HPLC | Lipid: Vcr | LSI | Diameter (nm) |
|---|---|---|---|---|---|---|
| Succinate | 19.1 | 7.13 | 0.054 | 228.5 | 2.9 | 257 |
| Pyrophosphate | 67.7 | 7.30 | 0.243 | 65.4 | 3.6 | 45 |
| Lactobionate | 90.3 | 7.41 | 0.335 | 48.6 | 4.5 | 55 |
| Citrate | 87.8 | 7.24 | 0.305 | 51.4 | 4.8 | 50 |
| Sulfate | 49.8 | 7.31 | 0.191 | 82.4 | 3.3 | 54 |
| Sucrose | NA | 5.85 | NA | NA | 3.8 | 40 |

One hundred thirteen $CD_2F_1$ female mice born on Oct. 15, 1992 were received on Nov. 24, 1992 from Charles River. Lymphosarcoma tumor cells (P1798, Dr. Joseph Mayo of the Tumour Repository in the Division of Cancer Treatment, NIH) were implanted ($1 \times 10^6$ intradermally) into their right flanks on day 0. The mice were randomized into 11 treatment groups and therapy was initiated four days after tumor implantation. The chemotherapeutic treatment groups consisted of free Vcr and nine vesicle-Vcr formulations (Vcr salts of glutamate, tartrate, hydrogen diphosphate, aspartate, EDTA, succinate, pyrophosphate, lactobionate, and citrate). Dosing was at 2.5 mg/kg. Tumor-bearing untreated controls received a treatment of 300 mM sucrose in a volume equivalent to the experimental groups. All mice were weighed three times a week for the first week and then twice weekly thereafter. Tumor size was measured with a caliper approximately once per week until death. Tumor volume was calculated from those measurements using the following formula: tumor volume=(length×width$^2$)/2. The percent increase in life span (% ILS) was defined as 100(median day of death of experimental group minus the median death of the control group) divided by the median day of death of the controls and the percent increase in survival (% T/C) was calculated as 100×(average day of death of the experimental group divided by the average day of death of the control group). The median survival time (MST) and the average survival time (AST) are displayed in Table 2. Survival time was recorded for each mouse and monitored for 27 days. The results of the efficacy study are presented in Table 2 & 3.

TABLE 2

Vcr Antitumor Efficacy

| Treatment | MST (Days) | AST | % ILS | % T/C |
|---|---|---|---|---|
| Sucrose Controls | 14 | 14.0 | NA | NA |
| Free Vcr | 14 | 14.4 | 0.0 | 102.9 |
| Vcr-Glutamate | 17 | 17.2 | 21.4 | 122.9 |
| Vcr-Tartrate | 16 | 16.2 | 14.3 | 115.7 |
| Vcr-H$_2$PO$_4$ | 17 | 16.7 | 21.4 | 119.3 |
| Vcr-Aspartate | 18 | 18.1 | 28.6 | 129.3 |
| Vcr-EDTA | 17 | 18.0 | 21.4 | 128.6 |
| Vcr-Succinate | 15 | 15.1 | 7.1 | 107.9 |
| Vcr-Pyrophosphate | 17 | 17.0 | 21.4 | 121.4 |
| Vcr-Lactobionate | 17 | 16.6 | 21.4 | 118.6 |
| Vcr-Citrate | 15 | 16.1 | 7.1 | 115.0 |

TABLE 3

Effect of Liposome Formulations on Tumor Volumes in $CD_2F_1$ Mice

| | Tumor size (mm$^3$) | | | | |
|---|---|---|---|---|---|
| Treatments | Day 5 | Day 7 | Day 11 | Day 14 | Day 17 |
| Sucrose Control | 70 | 169 | 1138 | 1558 | 1016 |
| Free Vcr | 50 | 78 | 623 | 1153 | Lethal |
| Vcr-Glutamate | 50 | 38 | 29 | 12 | 10 |
| Vcr-Tartrate | 48 | 34 | 48 | 28 | 0 |
| Vcr-Dihydrogen PO4 | 48 | 36 | 38 | 20 | 0 |
| Vcr-Aspartate | 36 | 31 | 31 | 21 | 0 |
| Vcr-EDTA | 47 | 35 | 35 | 15 | 0 |
| Vcr-Pyrophosphate | 35 | 34 | 37 | 29 | 10 |
| Vcr-Lactobionate | 48 | 40 | 37 | 14 | 16 |
| Vcr-Citrate | 53 | 37 | 45 | 27 | 11 |

The tumor size of the untreated controls is approximately 4.7 times the size of the average of the liposomal treatment groups by day 5 and increases to 34 times by day 11. In contrast, the average tumor size of the free Vcr treatment group is twice the size of the liposomal group and increases to 18.6 times for the same time period. For four groups, there were several long-term survivors (or "cures"), tartrate, dihydrogen phosphate, aspartate, and EDTA. Vesicle stability was monitored over time at 4° C. using the following parameters: (1) drug retention, (2) drug degradation, (3) vesicle turbidity, and (4) vesicle diameter. Drug retention was determined after passing 0.5 ml of liposomes over a PD-10 G25 column wherein the Vcr-entrapped vesicles were collected and assayed. The vesicle diameters and the light scattering index (LSI) were measured. Values less than 4.0 could reveal the presence of fused, flocculated, or aggregated vesicles, resulting in a higher turbidity. Vcr egress and integrity were assessed monthly. At zero time Vcr integrity ranged from 94.7 to 100.0 percent, and the lipid to drug ratio ranged from 48.6 to 82.36 except for Vcr-succinate which was 228.5. The median diameter of the major peak ranged from 45 to 55 nm for all vesicle preps except the succinate formulation. Five vesicle formulations displayed unimodal distributions. Six vesicle preps (tartrate, dihydrogen phosphate, aspartate, EDTA, lactobionate and citrate) displayed LSI values greater than four; three formulations had LSIs greater than 3 and the succinate formulation registered 2.9. By two weeks, only 2 vesicle formulations showed LSIs greater than 4, while seven were greater than 3; the succinate LSI remained unchanged. The median diameter of the major peak ranged from 53 to 60 nm, the succinate prep now registered 93 nm. By 4 weeks postincubation, the ratio of lipid to drug increased with all of the formulations, however, drug entrapment was greater than 100 with all formulations except citrate and succinate. All LSIs now ranged between 3.0 and 3.7 except the succinate formulation which approximated 2.8. The diameter of each major peak ranged between 47 and 59 nm.

All vesicle preparations showed a LSI value between 3.5 and 4.12 preload; however, all LSIs declined to less than 3 for all formulations except the lactobionate and citrate, which were 3.2. Removal of the extraneous counterion complexes of Vcr by gel filtration reduced aggregation. At zero hour six preps evinced LSIs higher than 4, while three preps ranged between 3.3 and 3.8. The LSI is a much more reliable index of vesicle aggregation than vesicle diameter because it considers all populations of the vesicle environment. The LSI's, however, declined from between 3.3 to 4.8 to 3.0–3.7 in 1 month. Three vesicle preps decreased in median diameter while six preps increased on average 5 to 9 nm.

EXAMPLE 2

This experiment details the tumor uptake of a neutral liposome formulation containing Vcr. Empty vesicles were prepared as in Example 1 using the following counterions: aspartate, glutamate, tartrate, pyrophosphate, dihydrogen phosphate, lactobionate, and citrate.

An aliquot of $^3$H Vcr (250 $\mu$Ci/ml) equivalent to 0.19 ml was evaporated to dryness under $N_2$. This was added to 0.6 ml of Vcr sulfate solution (10 mg/ml free base). Vcr liposomes were prepared as in Example 1.

The animal studies were conducted as in Example 1 except that treatment began six days after tumor implantation. Further, fifty-five animals were used with 3–5 animals per study group. Tumor tissues were processed according to the Pharmaceutics Protocol of August 1985 with one exception—processed tissues were assayed for radioactivity in a LKB Wallac 1219 Rackbeta Liquid Scintillation counter using a Bioflour quench curve for blood samples and an Econoflour quench curve consisting of a tissue matrix for solid tissues. The results are displayed in FIG. 1.

The eight counterions investigated in the first antitumor efficacy study were evaluated for their relative tumor uptake and/or retention of liposome delivered Vcr. Results are shown in FIG. 1. Of the counterions investigated, aspartic acid appeared to produce the greatest 24 hour accumulation of Vcr at the tumor site. Compared to free Vcr, aspartate resulted in more than 30-fold greater levels of drug in tumor at 24 h. Other counterions produced about a 10 to 15-fold increase in tumor Vcr levels relative to free drug. This superior increase in tumor uptake was surprising since it was not known that any particular counterion would have an effect on tumor uptake and that the mechanism in which any counterion would potentiate tumor uptake is not known. Any increase in tumor uptake by a particular counterion is therefore both unexpected, and to the degree in which aspartate increased tumor uptake, highly surprising.

Of the counterions investigated, aspartic acid appeared to produce the greatest 24 hour accumulation of Vcr at the tumor site. Compared to free Vcr, aspartate resulted in more than 30-fold greater levels of drug in tumor at 24 h. Other counterions produced about a 10 to 15-fold increase in tumor Vcr levels relative to free drug.

EXAMPLE 3

This example details the comparison of various lipid:drug ratios on toxicity and efficacy. Liposomes were prepared as in Examples 1 & 2 using the following counterions: lactobionate, aspartate, dihydrogen phosphate, glutamate, and tartrate. The prepared vesicles were tested at lipid:drug molar ratios of 50:1 and 100:1. The results indicated that decreased toxicity occurred at higher lipid to drug ratio but that the efficacy was comparable.

Although the above examples establish that the liposomal formulations provided a superior product it was desirable that a liposome formula be developed that would allow for less aggregation on storage. After about two weeks of storage the neutral liposomes began to slowly aggregate evidenced by a decrease in their LSI and an increase in median size or the growth of a second peak with larger diameter. In the following experiments a negatively charged lipid, distearoylphosphatidylglycerol (DSPG), was included in the liposomes as a means for preventing aggregation. It was surprisingly found that not only did the negatively charged liposomes not aggregate, but they showed superior efficacy than the neutral liposomes.

EXAMPLE 4

Preparation of vesicles was performed as follows:

Neutral vesicles.

DSPC:Chol (2:1) was hydrated in methyl ammonium aspartate (2000 mg lipid per 15 ml buffer) and sonicated 55–60 minutes at 65° C. The vesicles were annealed for ten minutes at 65° C. and cooled slowly to ambient temperature after which the vesicles were centrifuged at 150033 g. An aliquot (0.1 ml) of these vesicles was diluted 50% in methanol and the resulting mixture was spun for two minutes at $1.4 \times 10^4 \times g$. Aliquots from the organic and aqueous phases were spotted on Kieselgel F254 TLC plates and developed in chloroform:methanol: ammonium hydroxide (60:30:9 (5%)). Unentrapped buffer was removed by elution of a 12 ml volume of these vesicles using a 120 cm$^3$ (1 cm radius) Sephadex G-50 gel permeation column previously equilibrated with 300 mM sucrose. Vesicle suspension conductivity (11 $\mu$MHO) was measured with a YSI 35 Conductance meter. The vesicle sample was sterilized through a 0.2 $\mu$m pore filter and stored at room temperature until completion of Vcr loading. Vcr loading was performed at 64° C. for 10 minutes.

Negatively charged formulations.

DSPC:Chol:DSPG (2:1:0.1) vesicles were prepared as above except that unentrapped counterion was removed by gel filtration on 10 cm$^3$ PD-10 columns previously equilibrated with 300 mM sucrose. Aliquots (0.5 ml) were added to the columns and the vesicle fractions were collected. Two major fractions were collected and their conductivity measured at 16 and 726 $\mu$MHO respectively. To further reduce the unentrapped counterion concentration, one-half of the 726 $\mu$MHO sample was passed over a 90 cm$^3$ column (1 cm radius) prepared from the neutral Agarose resin. Fractions were collected and their conductivities measured. The various fractions were pooled to form three conductivity groups (30, 66, and 726 $\mu$MHO, respectively), sterilized and stored at room temperature until completion of lipid analyses and Vcr loading. Vcr free base was added to the preformed phospholipid vesicles to yield a lipid to drug ratio of 150:1 (w/w). Loading was performed at 64° C. for 10 minutes. Unentrapped Vcr was removed from the sonicated preparations by gel filtration using a Sephadex G50 Medium for the neutral formulation and A-5m for the charged formulation. The bed volume to vesicle preparation ratio ranged from 4 to 5. All preparations were diluted between 2.5 and 3. Unentrapped Vcr was removed from the homogenized preparations by ultrafiltration. All vesicle preparations were sterile-filtered through 0.2$\mu$Corning filters. Aliquots of each preparation were analyzed for LSI, size distribution, pH, and lipid and Vcr concentrations. Vcr analysis was performed by HPLC and by UV/VIS. Vesicle characteristics are displayed in Table 4.

TABLE 4

Vesicle Characteristics

| | Vcr (mg/ml) | Lipid (mg/ml) | Lipid Drug | Vcr % (entrapped) | pH | LSI | Median Diameter (nm) | Mean Volume (nm) |
|---|---|---|---|---|---|---|---|---|
| Charged | 0.250 | 31.03 | 124 | 97.2 | 6.9 | 3.91 | 50.2 | 53.8 |
| Neutral | 0.087 | 11.99 | 138 | 112.3 | 6.1 | 3.60 | 59.3 | 67.3 |

Female, $CD_2F_1$ mice (Charles River) were divided into four treatment groups of seven mice each for the therapy groups and two groups of six mice each for the non-therapy control and conventional drug groups. The animals were implanted with P-1798 lymphosarcoma cells ($1 \times 10^6$) into their right flanks four days prior to therapy. One dose level of conventional drug and two dose levels of Vcr liposomes (2.5 and 3.5 mg/kg) were administered intravenously four days after tumor implantation. Tumors were measured weekly with a caliper. All mice were monitored daily for survival. The results of the efficacy study are tabulated in Tables 5 & 6.

TABLE 5

SURVIVAL SUMMARY

| Group | Treatment | Mice N | Dose (mg/kg) | MST | % ILS | % T/C |
|---|---|---|---|---|---|---|
| 1 | Controls | 6 | 0 | 13 | NA | 100.0 |
| 2 | Free Vcr | 6 | 2.5 | 15 | 15.4 | 115.4 |
| 3 | S/−PG/ASP/ | 7 | 2.5 | 16 | 23.1 | 123.1 |
| 4 | S/−PG/ASP/ | 7 | 3.5 | 18 | 38.5 | 138.5 |
| 5 | S/+PG/ASP/ | 7 | 2.5 | 18 | 38.5 | 138.5 |
| 6 | S/+PG/ASP/ | 7 | 3.5 | 18 | 38.5 | 138.5 |

TABLE 6

Tumor Volume As A Function of Time

| Group | Treatment | Dose (mg/kg) | Day 7 | Day 11 | Day 14 |
|---|---|---|---|---|---|
| 1 | Controls | 0 | 248.8 (101.4) n = 6 | 901.9 (156.6) n = 6 | Lethal n = 0 |
| 2 | Free Vcr: | 2.5 | 130.0 (48.1) n = 6 | 497.7 (220.8) n = 6 | 924.1 (192.9)n n = 3 |
| 3 | S/−PG/ASP: | 2.5 | 55.2 (33.8) n = 7 | 22.0 (16.4) n = 7 | 13.3 (13.6) n = 6 |
| 4 | S/−PG/ASP: | 3.5 | 57.2 (29.5) n = 7 | 37.3 (17.6) n = 7 | 22.9 (14.3) n = 7 |
| 5 | S/+PG/ASP: | 2.5 | 54.0 (18.4) n = 7 | 25.3 (10.7) n = 7 | 14.7 (6.4) n = 7 |
| 6 | S/+PG/ASP: | 3.5 | 41.6 (21.7) n = 7 | 25.6 (11.4) n = 6 | 10.0 (6.7) n = 6 |

As can be gleaned from the tables, Vcr treatment increased survival times over untreated controls (MST of 13 days). Mice receiving free Vcr lived 1.15 times longer than the controls. The MST of mice treated with the Vcr liposomes ranged from 16 to 18 days. Tumor volume increased 181.2% in the nontreated controls over a 4 day period (day 7 to day 11). None of the animals survived beyond 14 days. In contrast, free Vcr reduced tumor volume by forty-eight percent of untreated controls by day 7 and forty-five percent on day 11. Treatment with Vcr entrapped vesicles reduced or arrested tumor growth.

Testing of sonicated preparations has demonstrated that inclusion of DSPG in VincaXome reduces aggregation without adversely affecting in vivo antitumor efficacy.

EXAMPLE 5

This example details the ability of negatively charged Vcr liposomes to be taken up by tumors. Methyl amine was used as the ion exchange component. Aspartate was used as the counterion.

Neutral vesicles were formed by hydrating a spray-dried powder of DSPC:Chol (2:1 molar ratio) in 150 mM methyl ammonium lactobionate (2000 mg lipid per 15 ml buffer with the pH at about 5.7. The vesicles were sonicated 55–60 minutes at 65° C., annealed 10 minutes at 65° C., cooled slowly to ambient temperature, and centrifuged for 10 minutes at 1500×g. Unentrapped buffer was removed by eluting 12 ml on a 120 cc Sephadex G-50 gel permeation column previously equilibrated with 300 mM sucrose. The vesicles were filtered through a 0.2 1 pore filter and stored at room temperature.

Charged vesicles comprised of DSPC:Chol:DSPG (2:1:0.1), were prepared as above except that unentrapped counterion was removed by gel filtration on 10 cc PD-10 columns (Sephadex G-25) previously equilibrated with 300 mM sucrose with the pH at about 5.5. Two major fractions were collected; their conductivities measured 16 and 726 $\mu$MHO, respectively. To further reduce the conductivity, one-half of the 726 $\mu$MHO sample was sized on a 90 cc column prepared from the neutral Agarose resin. Fractions were collected and their conductivities measured. The various fractions were pooled to form three conductivity groups (30, 66, and 726 $\mu$MHO, respectively), sterilized and stored at RT until completion of lipid analyses and Vcr loading.

The loading process was initiated by evaporating methanol from $^3$H Vcr (50 $C_i$ in 0.025M $H_2SO_4$, pH 4.3, Lot B99) under a gentle stream of nitrogen and the residue was diluted to 200 μl with water for injection (WFI). Aliquots (5 μl) were diluted to 100 μl and three 5 μl aliquots were counted for total radioactivity on a 1219 Spectral LB Wallac Rack beta Liquid Scintillation Counter (LSC). Radiolabeled Vcr (approximately 0.008 mg) was mixed with unlabeled Vcr (6.15 mg: from a solution containing 280 mg of Vcr from Ceres-lot VCU4/2B and 60 mg from Omni Chem, lot VCRS 252L); the Vcr specific activity was $1.623 \times 10^7$ DPM/mg at a Vcr concentration of 15.138 mg/ml. An aliquot of each empty vesicle preparation (200 mg) was mixed with 1.33 mg of $^3$H Vcr in 88 μl. The resulting preparations were heated for 12 minutes at 65° C. and cooled to ambient temperature.

Free Vcr was removed from each sample by gel filtration on A-5 m columns. The bed to vesicle volume ratio was 5 to 1. Three vesicle fractions were collected and aliquots were counted; greater than 97% of the radiolabeled Vcr was associated with fraction 2. Vcr entrapment measured between 46.4 to 77.9%. These samples were sterilized and the Vcr content remeasured by liquid scintillation counting. Vcr concentrations ranged between 0.068 and 0.152 mg/ml. The LSI, diameter and pH were measured three months after preparation.

LSI, pH and size distribution measured three months after vesicle preparation fell within normal ranges: LSIs≧3.8, pH≧6.0, and diameter between 58–76 nm.

Figure 2:
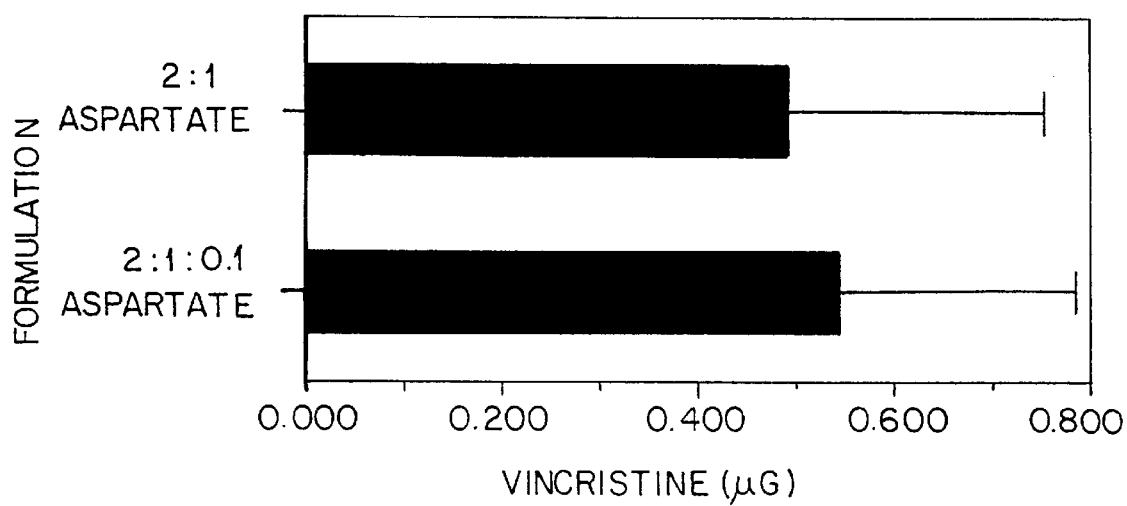
FIG. 2 displays the amount of vincristine taken up in the tumors of mice using negatively charge liposomes.

In the animal studies, thirty-two female $CD2F_1$ mice (Charles River, Wilmington, Del.) were divided into two treatment groups of eight mice for vesicle therapy. Lymphosarcoma tumor cells (P-1798) were implanted six days prior to therapy. The animals were shaved and $10^6$ cells were implanted intradermally into the right flank. Vesicle-entrapped Vcr was administered intravenously six days post tumor implantation. Mice with tumors between 50 to 100 mg and weighing between 17.2 and 23.6 grams were dosed at 2.5 mg/kg every three minutes. That dose was equivalent to 50 ng Vcr ($7-9 \times 10^5$ DPM) in 320–740 μl per 20 gram mouse. The mice were sacrificed by cervical dislocation twenty-four hours following injections. The mice were then dissected and tumors were excised for $^3$H Vcr -derived residues. Tissue samples were processed as stated in the Pharmaceutics Protocol of August 1985 with one exception—all processed tissues were assayed for radioactivity in a LKB Wallac 1219 Sectral Rackbeta Liquid Scintillation Counter. See FIG. 2.

Toxicity studies were also performed wherein the free Vcr was at least twice as toxic as the liposomal formulations. The negatively charged liposomes were stored at 4° C. and the vesicles remained stable for at least 8 months (LSI at about 4).

EXAMPLE 6

Negatively charged formulation was prepared as an example No. 4 using methol ammonium lactobionate in lipid:VCR ratios of 150:1, 100:1, and 50:1. The pH of final internal aqueous phase was adjusted from about pH 4 to about pH 9. The results are displayed in Table 7.

TABLE 7

| | % VCR Entrapped | | |
| --- | --- | --- | --- |
| | Lipid:Drug (Molar Ratio) | | |
| pH | 150 | 100 | 50 |
| 4.0 | 74.6 | 57.8 | 37 |
| 4.5 | 68.8 | 73 | 49.8 |
| 5.0 | 80.9, 106 | 84.8 | 55.3 |
| 5.5 | 93.7 | 90.1 | 53.3 |

TABLE 7-continued

| | % VCR Entrapped | | |
| --- | --- | --- | --- |
| | Lipid:Drug (Molar Ratio) | | |
| pH | 150 | 100 | 50 |
| 6.0 | 83.4, 83.2 | 80.1 | 57.9 |
| 6.5 | 87.3, 82 | 79 | 62.4 |
| 7.0 | 79.6 | 71 | 57.9 |
| 7.5 | 73.5 | 70.2 | 53.5 |
| 8.0 | 61.4 | | |
| 9.0 | 50.3 | | |

Table 7 shows a maximum range of loading at a final pH from about 5.0 up to about 6.0 with the maximum loading at about pH 5.5.

What is claimed is:

1. Liposomes having an internal aqueous phase, comprised of a phosphatidylcholine, a cholesterol and a phosphatidylglycerol in a ratio of about 2:1:0.01 to about 2:1:0.5 and having a mean size of less than 100 nm, wherein the liposomes further comprise a cationic vinca alkaloid and an anion of low membrane permeability selected from the group consisting of glutamate, tartrate, phosphate, EDTA, succinate, aspartate, pyrophosphate, lactobionate, citrate, and sulfate within the internal aqueous phase.

2. The composition of claim 1 wherein said phosphatidylcholine is selected from the group consisting of distearoyl phosphatidylcholine, dilauryl phosphatidylcholine, dipalmitoyl phosphatidylcholine, and dimiristoyl phosphatidylcholine.

3. The composition of claim 1 wherein said phosphatidylcholine is distearoyl phosphatidylcholine.

4. The composition of claim 1 wherein said phosphatidylglycerol is selected from the group consisting of distearoyl phosphatidylglycerol, dilauryl phosphatidylglycerol, dipalmitoyl phosphatidylglycerol, and dimiristoyl phosphatidylglycerol.

5. The composition of claim 1 wherein said phosphatidylglycerol is distearoyl phosphatidylglycerol.

6. The composition of claim 1 wherein the molar ratio of phosphatidylcholine, cholesterol and phosphatidylglycerol is 2:1:0.1.

7. The composition of claim 1 wherein said vinca alkaloid is selected from the group consisting of vincristine, vinblastine, vinleurosine, and vinrosidine.

8. The composition of claim 1 wherein said vinca alkaloid is vincristine.

9. The composition of claim 1 wherein the pH of the internal aqueous phase is from about 5 to about 8.

10. The composition of claim 1 wherein said anion is lactobionate.

11. The composition of claim 1 wherein said anion is aspartate.

12. A method for increasing accumulation of liposomes at a tumor site comprising administration of a liposomal composition having an internal aqueous phase comprising a phosphatidylcholine, a cholesterol and a phosphatidylglycerol in a ratio of about 2:1:0.01 to about 2:1:0.5 and having a mean size of less than 100 nm, wherein said composition further comprises a cationic vinca alkaloid and an anion of low membrane permeability selected from the group consisting of glutamate tartrate, phosphate EDTA, succinate, aspartate, pyrophosphate, lactobionate, citrate, and sulfate within said internal aqueous phase.

* * * * *